United States Patent
Fujiwara et al.

(10) Patent No.: US 12,310,743 B2
(45) Date of Patent: May 27, 2025

(54) SLEEP APNEA SYNDROME DETERMINATION APPARATUS, SLEEP APNEA SYNDROME DETERMINATION METHOD, AND SLEEP APNEA SYNDROME DETERMINATION PROGRAM

(71) Applicant: KYOTO UNIVERSITY, Kyoto (JP)

(72) Inventors: Koichi Fujiwara, Kyoto (JP); Chikao Nakayama, Kyoto (JP); Ayako Iwasaki, Kyoto (JP)

(73) Assignee: Kyoto University, Kyoto (JP)

( * ) Notice: Subject to any disclaimer, the term of this patent is extended or adjusted under 35 U.S.C. 154(b) by 249 days.

(21) Appl. No.: 17/430,424

(22) PCT Filed: Jan. 9, 2020

(86) PCT No.: PCT/JP2020/000529
§ 371 (c)(1),
(2) Date: Aug. 12, 2021

(87) PCT Pub. No.: WO2020/166239
PCT Pub. Date: Aug. 20, 2020

(65) Prior Publication Data
US 2022/0125376 A1      Apr. 28, 2022

(30) Foreign Application Priority Data
Feb. 13, 2019    (JP) .............................. 2019-023217

(51) Int. Cl.
*A61B 5/00*     (2006.01)
*A61B 5/08*     (2006.01)
*A61B 5/352*    (2021.01)

(52) U.S. Cl.
CPC ............. *A61B 5/4818* (2013.01); *A61B 5/08* (2013.01); *A61B 5/352* (2021.01); *A61B 5/7264* (2013.01)

(58) Field of Classification Search
CPC ......... A61B 5/4818; A61B 5/08; A61B 5/352; A61B 5/7264
See application file for complete search history.

(56) References Cited

U.S. PATENT DOCUMENTS

2021/0137452 A1    5/2021 Mitsukura et al.

FOREIGN PATENT DOCUMENTS

| CN | 109117730 A | * | 1/2019 | ............. A61B 5/349 |
| EP | 3632322 A1 |   | 4/2020 | |

(Continued)

OTHER PUBLICATIONS

R. K. Pathinarupothi, R. Vinaykumar, E. Rangan, E. Gopalakrishnan and K. P. Soman, "Instantaneous heart rate as a robust feature for sleep apnea severity detection using deep learning," 2017 IEEE EMBS International Conference, Orlando, FL, USA, 2017, pp. 293-29 (Year: 2017).*

(Continued)

*Primary Examiner* — Shirley X Jian
*Assistant Examiner* — Laura Hodge
(74) *Attorney, Agent, or Firm* — Millen, White, Zelano & Branigan P.C.; William F. Nixon

(57) ABSTRACT

A sleep apnea syndrome determination apparatus includes a processing unit configured to, by using RRI data indicating a heart rate interval (R-R Interval: RRI) in a sleeping period of a subject, determine whether or not the subject has sleep apnea syndrome. The processing unit operates to generate a feature vector including a plurality of heart rate intervals that are consecutive in the sleeping period; calculate, from a value that is outputted as a result of inputting the feature vector to a recurrent neural network and that is obtained for each identification target period that corresponds to the plurality of heart rate intervals included in the feature vector inputted, an index based on a ratio between a period of an (Continued)

apnea state and a period of a normal respiration state in the sleeping period; and determine whether the subject has sleep apnea syndrome, on the basis of the index.

6 Claims, 12 Drawing Sheets

(56) References Cited

FOREIGN PATENT DOCUMENTS

| JP | 2016214491 A | 12/2016 | | |
| --- | --- | --- | --- | --- |
| WO | WO-2009150765 A1 | * | 12/2009 | ............ A61B 5/0816 |
| WO | WO-2018221750 A1 | * | 12/2018 | ......... A61B 5/02405 |
| WO | WO-2019107012 A1 | * | 6/2019 | ............. A61B 5/024 |
| WO | WO-2020047750 A1 | * | 3/2020 | ............. A61B 5/349 |

OTHER PUBLICATIONS

D. Novak, K. Mucha and T. Al-Ani, "Long Short-Term Memory for apnea detection based on Heart Rate Variability," 2008 30th Annual International Conference of the IEEE Engineering in Medicine and Biology Society, Vancouver, BC, Canada, 2008, pp. 5234-5237, doi: 10.1109/IEMBS.2008.4650394. (Year: 2008).*

Xin Zhang and Weixuan Kou and Eric I-Chao Chang and He Gao and Yubo"Sleep Stage Classification Based on Multi-level Feature Learning and Recurrent Neural Networks via Wearable Device", 2017. (Year: 2017).*

B. Ballinger, J. Hsieh, A. Singh, N. Sohoni. J. Wang, G. Tison, G. Marcus, J. Sanchez, C. Maguire, J. Olgin, and M. Pletcher, "DeepHeart: Semi-Supervised Sequence Learning for Cardiovascular Risk Prediction", 2018. (Year: 2018).*

R. K. Pathinarupothi, D. P. J., E. S. Rangan, G. E.A., V. R. and K. P. Soman, "Single Sensor Techniques for Sleep Apnea Diagnosis Using Deep Learning," 2017 IEEE International Conference on Healthcare Informatics (ICHI), Park City, UT, USA, 2017, pp. 524-529, doi: 10.1109/ICHI.2017.37. (Year: 2017).*

English translation of International Search Report for PCT/JP2020/000529 dated Mar. 31, 2020.

Nakayama, C. et al. "Application of support vector machine to heart rate during sleep for sleep apnea syndrome screening," Proceedings of the 59th Annual Conference of the Institute of Systems, Control and Information Engineers, Osaka, May 20-22, 2015.

English Machine Translation for JP2016214491, Publication Date: Dec. 22, 2016.

Office Action issued Oct. 17, 2023J in corresponding Japanese Application No. JP2020-572122 (pp. 1-3) and English machine translation thereof (pp. 1-3).

* cited by examiner

FIG. 5

| DETERMINATION METHOD | INPUT VALUE | IDENTIFICATION MODEL | INPUT METHOD |
|---|---|---|---|
| FIRST TECHNIQUE | RRI | LSTM | VARIABLE LENGTH VECTOR |
| SECOND TECHNIQUE | RRI | simple RNN | VARIABLE LENGTH VECTOR |
| THIRD TECHNIQUE | RRI | LSTM | FIXED LENGTH VECTOR |
| FOURTH TECHNIQUE | HRV INDEX | SVM | VARIABLE LENGTH VECTOR |
| FIFTH TECHNIQUE | HRV INDEX | LSTM | VARIABLE LENGTH VECTOR |

FIG. 6

|  |  | MALE | | | FEMALE | | |
| --- | --- | --- | --- | --- | --- | --- | --- |
|  |  | AHI 0-14 | AHI 15-29 | AHI 30- | AHI 0-14 | AHI 15-29 | AHI 30- |
| AGE | 18-30 | 7 | 0 | 0 | 15 | 0 | 1 |
|  | 31-50 | 7 | 2 | 5 | 6 | 0 | 0 |
|  | 51-80 | 0 | 7 | 7 | 0 | 1 | 1 |

FIG. 12

| EVALUATION VALUE | DETERMINATION METHOD | | | | |
|---|---|---|---|---|---|
| | FIRST TECHNIQUE | SECOND TECHNIQUE | THIRD TECHNIQUE | FOURTH TECHNIQUE | FIFTH TECHNIQUE |
| SENSITIVITY SE | 100 | 100 | 91 | 82 | 91 |
| SPECIFICITY SP | 100 | 94 | 82 | 82 | 88 |
| POSITIVE REACTION PREDICTIVE VALUE | 100 | 92 | 77 | 75 | 83 |
| NEGATIVE REACTION PREDICTIVE VALUE | 100 | 100 | 93 | 86 | 94 |

SLEEP APNEA SYNDROME DETERMINATION APPARATUS, SLEEP APNEA SYNDROME DETERMINATION METHOD, AND SLEEP APNEA SYNDROME DETERMINATION PROGRAM

TECHNICAL FIELD

The present disclosure relates to a sleep apnea syndrome determination apparatus, a sleep apnea syndrome determination method, and a sleep apnea syndrome determination program. This application claims priority on Japanese Patent Application No. 2019-023217 filed on Feb. 13, 2019, the entire content of which is incorporated herein by reference.

BACKGROUND ART

Sleep apnea syndrome (SAS) is a disease in which respiration stops or the respiratory volume decreases during sleep (hereinafter, this state is also referred to as apnea). Specifically, sleep apnea syndrome is a symptom in which apnea occurs not less than 30 times during 7-hour sleep, or not less than 5 times per hour. Apnea means an airflow stop state of not less than 10 seconds that occurs during sleep.

CITATION LIST

Patent Literature

PATENT LITERATURE 1: Japanese Laid-Open Patent Publication No. 2016-214491

SUMMARY OF INVENTION

In PATENT LITERATURE 1, a heart rate variability (HRV) index is calculated from heart rate data, of a subject, that is obtained by a heart rate measuring instrument, and on the basis of the heart rate variability index, whether the subject has apnea, hypopnea, or normal respiration is identified for each predetermined period during sleep. Accordingly, temporal variation of the respiratory state of the subject can be known.

SAS brings about excessive drowsiness and decrease in concentration power during daytime, and thus, can be a risk factor of traffic accidents. In addition, it is known that SAS can be a cause of various lifestyle diseases and severe conditions thereof and can cause cardiovascular disorder, glucose metabolism disorder, lipid metabolism disorder, and the like. Therefore, it is desired that whether or not the subject has SAS is determined with high accuracy.

Therefore, the inventors of the present application have applied the technique of determining the respiratory state for each predetermined period during a sleeping period as in PATENT LITERATURE 1, thereby further proposing a technique that enables high accuracy determination of whether or not the subject has SAS.

According to an embodiment, a sleep apnea syndrome determination apparatus includes: a processing unit configured to, by using RRI data indicating a heart rate interval (R-R Interval: RRI) in a sleeping period of a subject, determine whether or not the subject has sleep apnea syndrome. The processing unit is configured to operate so as to generate a feature vector including a plurality of heart rate intervals that are consecutive in the sleeping period, calculate, from a value that is outputted as a result of inputting the feature vector to a recurrent neural network and that is obtained for each identification target period that corresponds to the plurality of heart rate intervals included in the feature vector inputted, an index based on a ratio between a period of an apnea state and a period of a normal respiration state in the sleeping period, and determine whether or not the subject has sleep apnea syndrome, on the basis of the index.

A sleep apnea syndrome determination method according to another embodiment is for, by using RRI data indicating a heart rate interval in a sleeping period of a subject, determining whether or not the subject has sleep apnea syndrome. The sleep apnea syndrome determination method includes: a step of generating a feature vector including a plurality of heart rate intervals that are consecutive in the sleeping period; a step of calculating, from a value that is outputted as a result of inputting the feature vector to a recurrent neural network and that is obtained for each identification target period that corresponds to the plurality of heart rate intervals included in the feature vector inputted, an index based on a ratio between a period of an apnea state and a period of a normal respiration state in the sleeping period; and a step of determining whether or not the subject has sleep apnea syndrome, on the basis of the index.

A non-transitory computer storage medium encoded with a sleep apnea syndrome determination program according to another embodiment is configured to cause a computer to execute a process of, by using RRI data indicating a heart rate interval in a sleeping period of a subject, determining whether or not the subject has sleep apnea syndrome. The sleep apnea syndrome determination program causes the computer to execute: a step of generating a feature vector including a plurality of heart rate intervals that are consecutive in the sleeping period; a step of calculating, from a value that is outputted as a result of inputting the feature vector to a recurrent neural network and that is obtained for each identification target period that corresponds to the plurality of heart rate intervals included in the feature vector inputted, an index based on a ratio between a period of an apnea state and a period of a normal respiration state in the sleeping period; and a step of determining whether or not the subject has sleep apnea syndrome, on the basis of the index.

BRIEF DESCRIPTION OF DRAWINGS

FIG. 5 shows determination conditions of respective techniques evaluated in an evaluation test by the inventors.

FIG. 6 shows attributions of subjects in the evaluation test.

FIG. 12 shows evaluation values of the determination result according to each technique in the evaluation test.

DESCRIPTION OF EMBODIMENTS

Figure 1:
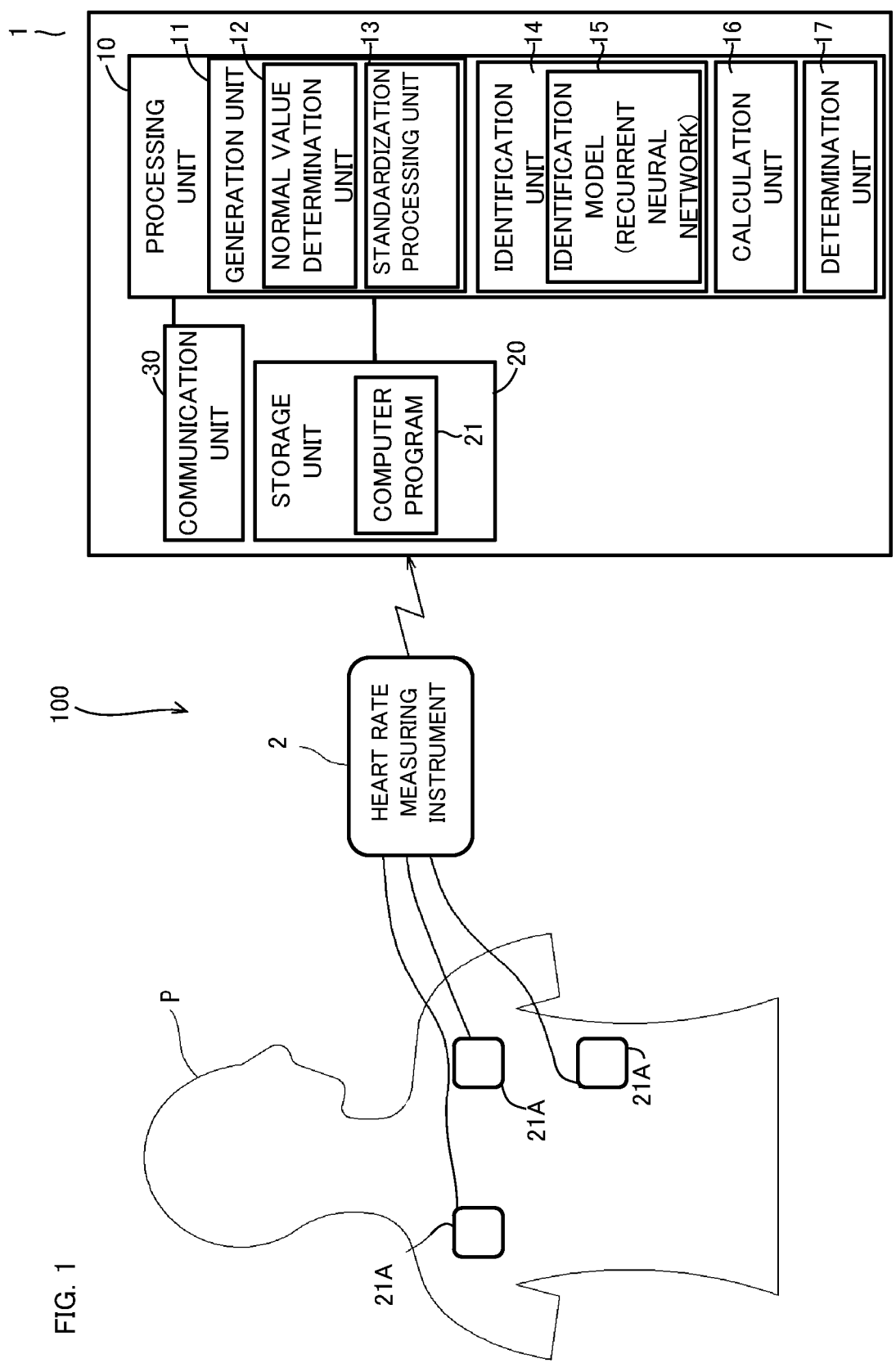
FIG. 1 shows an outline of a configuration of a system including a sleep apnea determination apparatus (hereinafter, determination apparatus) according to an embodiment.

[1. Outline of Sleep Apnea Syndrome Determination Apparatus, Sleep Apnea Syndrome Determination Method, and Sleep Apnea Syndrome Determination Program]

(1) A sleep apnea syndrome determination apparatus included in the present embodiment includes: a processing unit configured to, by using RRI data indicating a heart rate interval (R-R Interval: RRI) in a sleeping period of a subject, determine whether or not the subject has sleep apnea syndrome. The processing unit is configured to operate so as to generate a feature vector including a plurality of heart rate intervals that are consecutive in the sleeping period, calculate, from a value that is outputted as a result of inputting the feature vector to a recurrent neural network and that is obtained for each identification target period that corresponds to the plurality of heart rate intervals included in the feature vector inputted, an index based on a ratio between a period of an apnea state and a period of a normal respiration state in the sleeping period, and determine whether or not the subject has sleep apnea syndrome, on the basis of the index.

As a result of an evaluation test performed by the inventors of the present application, it has been verified that, when a recurrent neural network is adopted as the identification model, the determination accuracy is significantly improved when compared with a case where an index value calculated from the heart rate intervals is inputted to an identification model other than the recurrent neural network. Therefore, this sleep apnea syndrome determination apparatus can determine an SAS patient with high accuracy.

(2) Preferably, the recurrent neural network has learned through machine learning in advance so as to output, in response to the feature vector having been inputted, a value indicating a sleep state in the identification target period. As a result of the evaluation test performed by the inventors of the present application, the following has been verified. That is, when a feature vector that includes a plurality of heart rate intervals in the identification target period is used as an input value, and a recurrent neural network that has learned through machine learning in advance so as to output, in response to the feature vector having been inputted, a value indicating a sleep state in the identification target period is adopted, the determination accuracy is significantly improved when compared with a case where an index value calculated from the heart rate intervals is inputted to an identification model other than the recurrent neural network. Therefore, this sleep apnea syndrome determination apparatus can determine an SAS patient with high accuracy.

(3) Preferably, the recurrent neural network is LSTM (Long Short-Term Memory). As a result of an evaluation test performed by the inventors of the present application using LSTM, which is known to have high performance among recurrent neural networks, it has been verified that using LSTM as the recurrent neural network further improves the determination accuracy.

(4) Preferably, the identification target period has a fixed period length, and the feature vector is a variable length vector formed as a time series of a group of pieces of RRI data respectively indicating the plurality of heart rate intervals in the identification target period. As a result of the evaluation test performed by the inventors of the present application, it has been verified that using the feature vector having a variable length improves the determination accuracy when compared with using the feature vector having a fixed length.

(5) Preferably, when inputting the feature vector to the recurrent neural network, the processing unit is not configured to input, to the recurrent neural network, the feature vector that has been generated from the plurality of heart rate intervals that include a heart rate interval greater than a threshold indicating an abnormal value of a heart rate interval. Accordingly, only a feature vector generated from only the heart rate intervals that have been determined as having normal values as a result of determination (normal value determination) of whether or not the input value is a normal value, is inputted to the recurrent neural network. As a result of the evaluation test performed by the inventors of the present application, it has been verified that the determination accuracy is more improved by performing the normal value determination.

(6) Preferably, the generating of the feature vector includes standardizing a value of each of the plurality of heart rate intervals. Accordingly, individual differences among subjects are eliminated, and the determination accuracy can be improved.

(7) Preferably, the index is a ratio of the period of the apnea state to the sleeping period, and in the determining step, when the ratio is greater than a threshold indicating sleep apnea syndrome, the subject is determined to have sleep apnea syndrome. Accordingly, whether or not the subject has SAS can be easily determined.

(8) A sleep apnea syndrome determination method included in the present embodiment is for, by using RRI data indicating a heart rate interval in a sleeping period of a subject, determining whether or not the subject has sleep apnea syndrome. The sleep apnea syndrome determination method includes: a step of generating a feature vector including a plurality of heart rate intervals in an identification target period in the sleeping period; a step of inputting the feature vector to a recurrent neural network having learned through machine learning in advance so as to output, in response to a feature vector having been inputted, a value indicating a sleep state in an identification target period that corresponds to a plurality of heart rate intervals included in the feature vector; a step of calculating, from a value, for each identification target period, that is outputted from the recurrent neural network in response to the input, an index based on a ratio between a period of an apnea state and a period of a normal respiration state in the sleeping period; and a step of determining whether or not the subject has sleep apnea syndrome, on the basis of the index. This method is the determination method performed in the sleep apnea syndrome determination apparatus according to (1) to (7). Therefore, this method exhibits the same effects as those of the sleep apnea syndrome determination apparatus according to (1) to (7).

(9) A non-transitory computer storage medium encoded with a sleep apnea syndrome determination program included in the present embodiment is configured to cause a computer to execute a process of, by using RRI data indicating a heart rate interval in a sleeping period of a subject, determining whether or not the subject has sleep apnea syndrome. The sleep apnea syndrome determination program causes the computer to execute: a step of generating a feature vector including a plurality of heart rate intervals that are consecutive in the sleeping period; a step of inputting the feature vector to a recurrent neural network having learned through machine learning in advance so as to output, in response to a feature vector having been inputted, a value indicating a sleep state in an identification target period that corresponds to a plurality of heart rate intervals included in the feature vector; a step of calculating, from a value, for each identification target period, that is outputted from the recurrent neural network in response to the input, an index based on a ratio between a period of an apnea state and a period of a normal respiration state in the sleeping period; and a step of determining whether or not the subject has sleep apnea syndrome, on the basis of the index. With this program, a computer can be caused to function as the sleep apnea syndrome determination apparatus according to (1) to (7). Therefore, this program exhibits the same effects as those of the sleep apnea syndrome determination apparatus according to (1) to (7).

[2. Examples of Sleep Apnea Syndrome Determination Apparatus, Sleep Apnea Syndrome Determination Method, and Sleep Apnea Syndrome Determination Program]

A system 100, shown in FIG. 1, including a sleep apnea determination apparatus 1 according to the present embodiment includes the sleep apnea determination apparatus (hereinafter, referred to as a "determination apparatus") 1 and a heart rate measuring instrument 2. The determination apparatus 1 and the heart rate measuring instrument 2 are communicable with each other. The communication may be wireless communication or may be wired communication.

The heart rate measuring instrument 2 is a small, lightweight wearable terminal that is attached to the body of a subject P and that is for measuring the heart rate of the subject P. The heart rate measuring instrument 2 has connected thereto a plurality of (three in FIG. 1) electrodes 21A that are attached to the body surface of the subject P. The three electrodes 21A are, for example, a positive electrode, a negative electrode, and a ground electrode. An example of the wearable terminal functioning as the heart rate measuring instrument 2 is a smartwatch that has a heart rate measuring function. The wearable terminal itself may function as the determination apparatus 1 and the heart rate measuring instrument 2.

Figure 2:
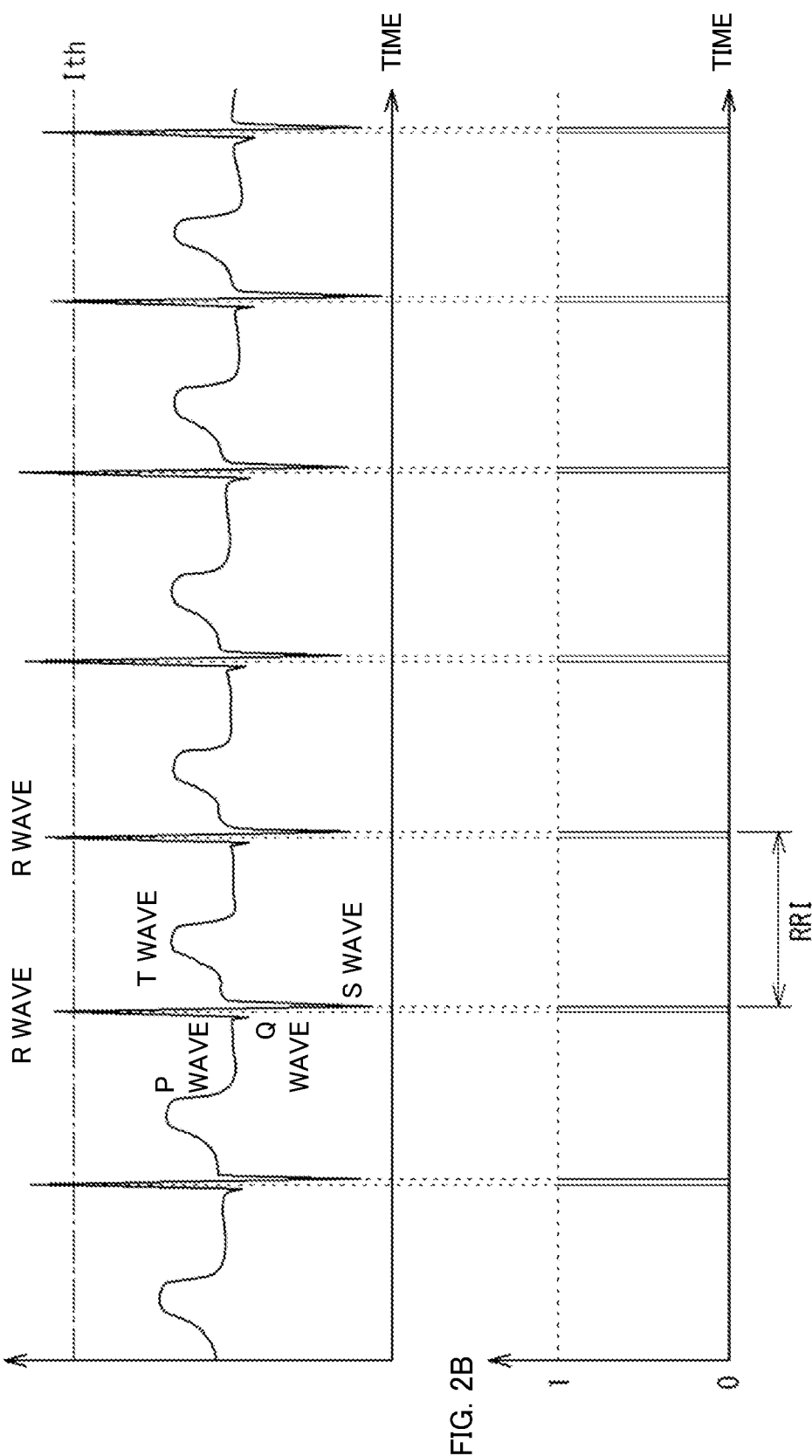
FIG. 2A shows an example of an electrocardiographic signal.
FIG. 2B shows R wave data.

In FIG. 2A, the vertical axis represents electric potential and the horizontal axis represents time. When a heart rate is measured by using the electrodes 21A, electric potential change in the form of P to T waves cyclically appears in an electrocardiographic signal as shown in FIG. 2A. A peak that has a highest electric potential in the electric potential change in a unit cycle is referred to as an R wave, and the ventricular myocardium contracts at the timing of the R wave. The heart rate measuring instrument 2 transmits heart rate data to the determination apparatus 1. An example of the heart rate data is RRI data. The RRI data indicates an RRI (R-R Interval).

The RRI is a feature value obtained from the R wave. The RRI data corresponding to the electrocardiographic signal in FIG. 2A indicates the RRI, which is each interval between the R waves, in a rectangular pulse train in which "1" is set for the period (a period in which a signal intensity I exceeds a predetermined intensity threshold Ith) that corresponds to the R wave in the electrocardiographic signal, and "0" is set for the other periods, as shown in FIG. 2B.

The determination apparatus 1 receives RRI data in a sleeping period of the subject P transmitted from the heart rate measuring instrument 2, and executes a determination process by using the RRI data, thereby determining whether or not the subject P has sleep apnea syndrome.

As another example, the heart rate data transmitted from the heart rate measuring instrument 2 may be data that indicates a numerical value group that represents an electrocardiographic waveform or the electrocardiographic waveform itself. In this case, the determination apparatus 1 calculates the RRI from the data received from the heart rate measuring instrument 2, and uses the calculated RRI in the determination process described later.

As shown in FIG. 1, the determination apparatus 1 is implemented as a computer including a processing unit 10 and a storage device 20. The storage device 20 is connected to the processing unit 10. The processing unit 10 is a CPU (Central Processing Unit), for example. The determination apparatus 1 also includes a communication unit 30 for performing communication with the heart rate measuring instrument 2. The communication unit 30 may be a communication mechanism for short-range wireless communication such as Bluetooth (registered trademark), or may be a communication mechanism for wireless LAN (Local Area Network). The communication unit 30 is connected to the processing unit 10. The communication unit 30 functions as an input unit for inputting heart rate data from the heart rate measuring instrument 2.

Preferably, the computer implementing the determination apparatus 1 is a mobile terminal, such as a smartphone or a tablet, for example. This is preferable because the mobile terminal of the subject P can be utilized as the determination apparatus 1. The mobile terminal may be a wearable device such as a smartwatch. The determination apparatus 1 may be implemented by a plurality of computers. For example, the determination apparatus 1 may be implemented as a combination of a plurality of mobile terminals. An example of the plurality of mobile terminals is a smartphone and a smartwatch.

The computer implementing the determination apparatus 1 may be a server computer on a network such as the Internet. In this case, the RRI data transmitted from the heart rate measuring instrument 2 of the subject P is transmitted to the server computer via a network such as the Internet. When the server computer determines whether or not the subject has sleep apnea syndrome, the server computer may notify a terminal (mobile terminal, etc.) of the subject P via the network.

The storage device 20 of the determination apparatus 1 has stored therein a computer program 21 for causing the processing unit 10 to execute the determination process. As a result of the processing unit 10 executing the computer program 21, the computer functions as the determination apparatus 1.

The determination process is a process of determining whether or not the subject P has sleep apnea syndrome, by using the RRI data in the sleeping period of the subject P. The determination process includes a generation process, an identification process, and a calculation process.

The generation process is a process of generating a feature vector from an RRI data group of a predetermined period in a sleeping period. The feature vector is used as an input value in the identification process described later, and is a single vector obtained by putting together a plurality of features indicating the sleep state of the subject in the aforementioned predetermined period. The processing unit 10 functions as a generation unit 11, which executes the generation process. That is, a prescribed period is set as an identification target period, which is a target period for the identification process described later, and RRIs from an electrocardiographic waveform measured in the identification target period are arranged in time series, to obtain a feature vector.

The number of RRIs measured in the identification target period, which is a fixed period, is not a constant number. Thus, the number of elements of the feature vector is variable. That is, the feature vector that is generated is a variable length vector. When the electrocardiographic waveform shown in FIG. 3 has been measured by the heart rate measuring instrument 2 with respect to periods T1, T2, and RRI data has been obtained, the generation unit 11 generates feature vectors FV1, FV2 in the periods T1, T2 as shown below.

FV1={925, 905, . . . , 885}

FV2={935, 915}

Preferably, the generation process includes a normal value determination process of determining whether or not each RRI has a normal value. The generation unit 11 includes a normal value determination unit 12, which executes the normal value determination process. The normal value determination unit 12 has stored therein in advance a threshold (e.g., 2000 msec) for RRI, and compares each RRI with the threshold to determine whether the RRI is abnormal or normal. An abnormal value of the RRI occurs due to a factor such as artifact, for example. The generation unit 11 generates a feature vector only for, among the identification target periods in the sleeping period, an identification target period in which all the RRIs included therein have been determined to be normal, and the generation unit 11 does not generate a feature vector for an identification target period in which even a single abnormal RRI is included. Alternatively, among generated feature vectors, a feature vector of an identification target period in which even a single RRI has been determined to be abnormal is not used as a feature vector in the determination process. As a result of the normal value determination, each generated feature vector does not include an abnormal value. That is, only feature vectors that are each composed of RRIs having normal values are used in the determination process. As a result, determination accuracy can be improved.

As the feature vector generation method, a method of generating a feature vector by using a fixed number of consecutive RRIs may be adopted. In this case, the number of elements of the feature vector is constant, and the feature vector has a fixed length. In contrast, the identification target period has a variable length.

In this case, when an abnormal value due to a premature beat is included in the fixed number of consecutive RRIs, the premature beat itself is counted as one heartbeat. Therefore, the identification target period corresponding to the fixed number of RRIs becomes shorter than the identification target period when the premature beat does not occur.

When taking this into consideration, in the determination apparatus 1, it is preferable to, rather than to use a fixed number of RRIs, generate a feature vector having a variable length from a plurality of consecutive RRIs included in an identification target period that is a fixed-length period, and use the generated feature vector in the determination process. In a case where the feature vector has a variable length, a recurrent neural network (hereinafter, also referred to as RNN) in which a variable length vector can be inputted is used as an identification model.

Preferably, the generation process includes a standardization process of standardizing an RRI group of each identification target period. The generation unit 11 includes a standardization processing unit 13, which executes the standardization process. The standardization process is, for example, a normalization process, and is a process in which, for example, an RRI group of the identification target period is converted, by using the formula below, to data in which the mean of the RRIs in a predetermined period is 0 and the variance thereof is 1. Accordingly, individual differences among subjects are eliminated, and the determination accuracy can be improved.

$$zi=(xi-\mu)/\sigma$$

($xi$ represents each RRI, $\mu$ represents a mean value, and $\sigma$ represents a standard deviation).

As another example of the feature vector, a vector composed of a plurality of HRV indexes is also conceivable. The HRV indexes can be two or more indexes among (1) to (11) below, for example. As an example, identification of the sleep state using the HRV index is performed in a determination technique in which: whether the subject has apnea or normal respiration is identified for each time period during sleep; and temporal variation indicating whether the subject has apnea or normal respiration is obtained. This determination technique uses, as an example of an identification model, a support vector machine that discriminates between an apnea state and a normal respiration state when given an HRV index.

(1) mean NN: Mean of RRI.

(2) SDNN: Standard deviation of RRI.

(3) Total Power: Total power spectrum of RRI.

(4) RMSSD: Square root of the mean value of the square of the difference between the n-th RRI and the n+1-th RRI. When the variation of RRI is large, the value becomes large, and RMSSD serves as an index of activity of the autonomic nervous system.

(5) NN50: The number of cases in which the difference between the n-th RRI and the n+1-th RRI exceeds 50 milliseconds. Ordinary RRI variation is not greater than 50 milliseconds, and NN50 serves as an index of significant variation.

(6) pNN50: Proportion of the value of NN50 to the number of all R waves. NN50 is the number of times, and thus, in general, when the window width is long, NN50 has a large value. When pNN50 is taken into consideration, the proportion of occurrence of large variation can be grasped.

(7) LF: Power spectrum in a frequency band of an LF band (0.04 Hz to 0.15 Hz). LF is mainly used as an index of activity of the sympathetic nervous system.

(8) HF: Power spectrum in a frequency band of an HF band (0.15 Hz to 0.4 Hz). HF is mainly used as an index of activity of the parasympathetic nervous system.

(9) LF/HF: The ratio between LF and HF, defined as LF/HF. LF/HF is considered to be the ratio of the activity states between the sympathetic nervous system and the parasympathetic nervous system. LF/HF has a large value when the sympathetic nerve is dominant, and has a small value when the parasympathetic nerve is dominant.

(10) LFnu: Corrected LF defined as LF/(LF+HF). LFnu emphasizes change in sympathetic nerve activity.

(11) HFnu: Corrected HF defined as HF/(LF+HF). HFnu emphasizes change in parasympathetic nerve activity.

Here, each RRI is a value directly obtained from an electrocardiographic waveform of the subject, and consecutive RRIs can be said to be a value group directly representing the feature of the electrocardiographic waveform in the sleeping period of the subject. The inventors analyzed that since each HRV index is an index calculated from RRIs and a value relevant to RRIs, the HRV index does not provide direct representation when compared with RRIs.

Therefore, based on this analysis, the inventors decided to generate a feature vector from RRIs themselves, and to use the generated feature vector in the identification process described later. Accordingly, a more direct feature of the electrocardiographic waveform than when a feature vector generated from the HRV indexes is used will be used in the identification process described later. As a result, the determination accuracy can be improved.

The identification process is a process of identifying, for each identification target period, whether the sleep state is an apnea state or a normal state. The processing unit 10 functions as an identification unit 14, which executes the identification process. The identification unit 14 includes an identification model 15. The identification model 15 has learned through machine learning in advance so as to output, in response to a feature vector having been inputted, a value indicating a sleep state in an identification target period that corresponds to the feature vector.

Figure 3:
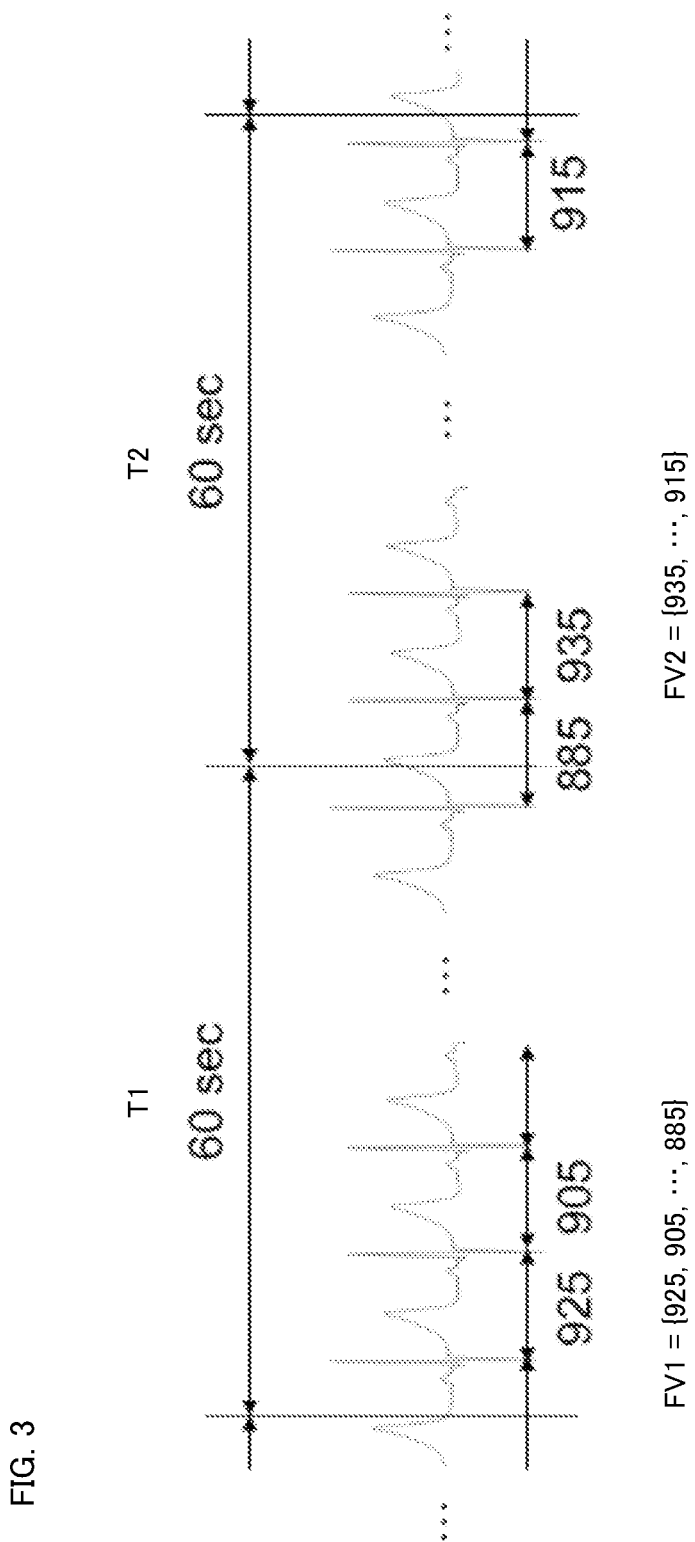
FIG. 3 illustrates a feature vector.

For example, when the feature vectors FV1, FV2 shown in FIG. 3 are each assumed to be a learning feature vector, the identification model 15 has learned so as to output, for example, "1" indicating an apnea state and "0" indicating a normal respiration state, in response to an input of each of the feature vectors FV1, FV2. The apnea state means a state of apnea or hypopnea. The state of apnea is defined as a state where ventilation stops for not less than 10 seconds. The state of hypopnea is defined as a state where a state of 50% or more decrease of a respiration airflow continues for not less than 10 seconds. Accordingly, for each identification target period, an output of a value indicating a respiratory state is obtained.

In the determination apparatus 1, a recurrent neural network (RNN) is used as the identification model 15. Examples of RNN include Simple RNN (simple recurrent neural network), LSTM (Long Short-Term Memory), GRU (Gated Recurrent Unit), Bi-directional RNN, Attention RNN, and QRNN (Quasi-Recurrent neural network).

Another example of the identification model different from RNN is SVM (Support Vector Machine). SVM is used in the above-mentioned PATENT LITERATURE 1. Therefore, it is also conceivable to use, as the identification model 15, a model, such as SVM, that is not RNN.

Here, RNN is, among neural networks, a model in which an output of a certain layer in a middle layer from an input value to an output value is used as an input for a middle layer from the next input value to output value. In other words, RNN is a neural network that has a recurrent structure in which an output of a neural network is used as an input of another network. In RNN, middle layers are linearly connected to each other along time series. Therefore, in RNN, an input value at a certain time point influences an output value for an input value after the time point. That is, RNN is a model that performs prediction on the basis of past data, in other words, performs learning based on time series data. This is different from a model, such as SVM, that is not RNN.

In this regard, in the determination apparatus 1, a feature vector configured by arranging RRIs of each identification target period in time series is inputted to the identification model 15. Therefore, an input value to the identification model 15 has temporal continuity. Since consecutive RRIs are values that consecutively represent the sleep state of the subject, the consecutive RRIs have relevance in terms of time series. Thus, the inventors reached a conclusion that, when such a feature vector is used, RNN that performs learning based on time series data outputs a value corresponding to continuous vital reaction with higher accuracy, than a model, such as SVM, that is not RNN. Therefore, the inventors decided to use RNN as the identification model 15.

The identification unit 14 inputs a feature vector for each predetermined period in the sleeping period to the identification model 15, and obtains an output of a value for each identification target period from the identification model 15. The value for each identification target period is, for example, "1" representing the apnea state and "0" representing the normal respiration state described above.

In the calculation process, an index based on a ratio between a period of the apnea state and a period of the normal respiration state in the sleeping period is calculated. The processing unit 10 functions as a calculation unit 16, which executes the calculation process. The index is, for example, an AS (Apnea/Sleep) ratio A, which is represented by the formula below and which is the ratio of a period ta of the apnea state to a sleeping period t. The period ta of the apnea state is the total of identification target periods identified as corresponding to the apnea state. The index is not limited to the AS ratio. Another example of the index may be a ratio of a period of the apnea state to a period of the normal respiration state.

$$A = ta/t \times 100 [\%]$$

In the determination process, whether or not the subject P has SAS is determined on the basis of comparison between the calculated index value (AS ratio) A of the index and a threshold TH that allows determination of SAS. The processing unit 10 functions as a determination unit 17, which performs this determination. When the AS ratio A is not less than the threshold TH (A≥TH), the determination unit 17 determines that the subject P has SAS. When the AS ratio A is less than the threshold TH (A<TH)), the determination unit 17 determines that the subject P does not have SAS. Use of the AS ratio A facilitates determination of whether or not the subject P has SAS.

A user (subject P) of the system 100 attaches the heart rate measuring instrument 2 to the body, disposes the determination apparatus 1 at a position, such as bedside, where the determination apparatus 1 can communicate with the heart rate measuring instrument 2, and sleeps. Then, in the determination apparatus 1, whether or not the subject P has SAS is determined according to the method shown in the flow chart in FIG. 4.

Figure 4:
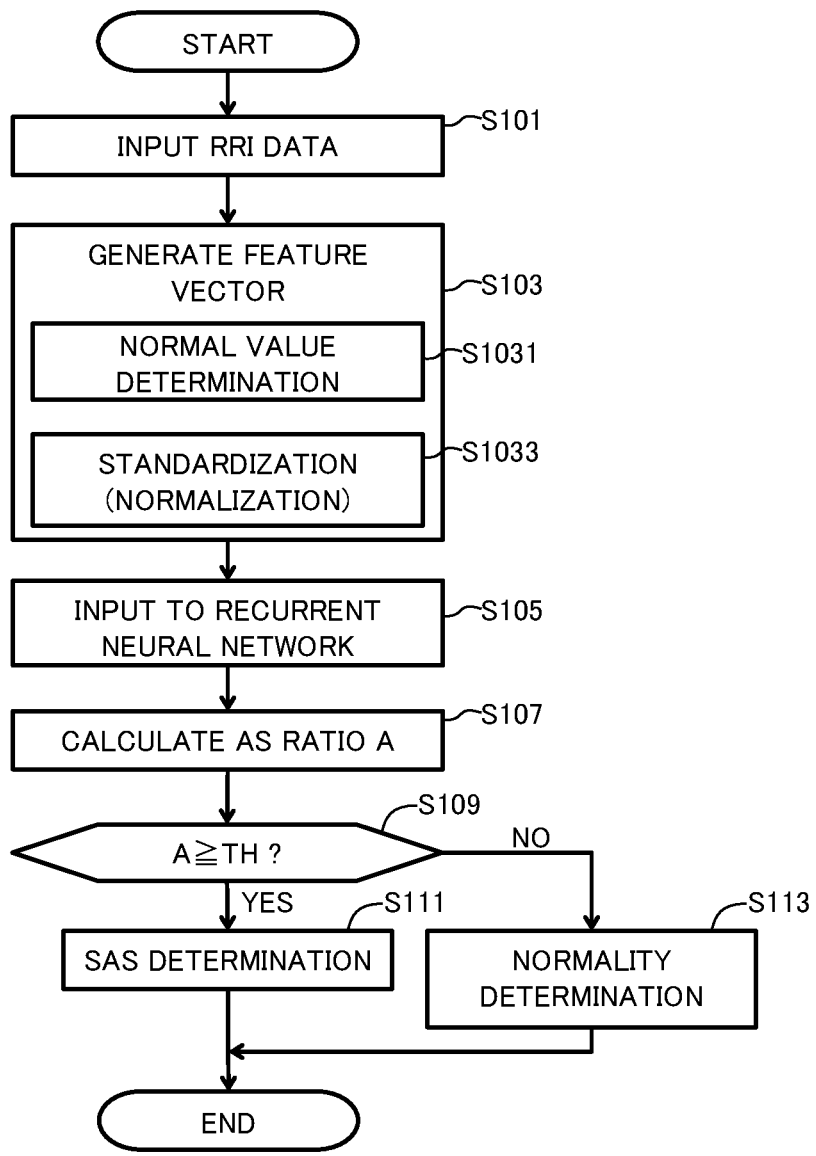
FIG. 4 is a flow chart showing a flow of a determination process performed in the determination apparatus.
Figure 7A:
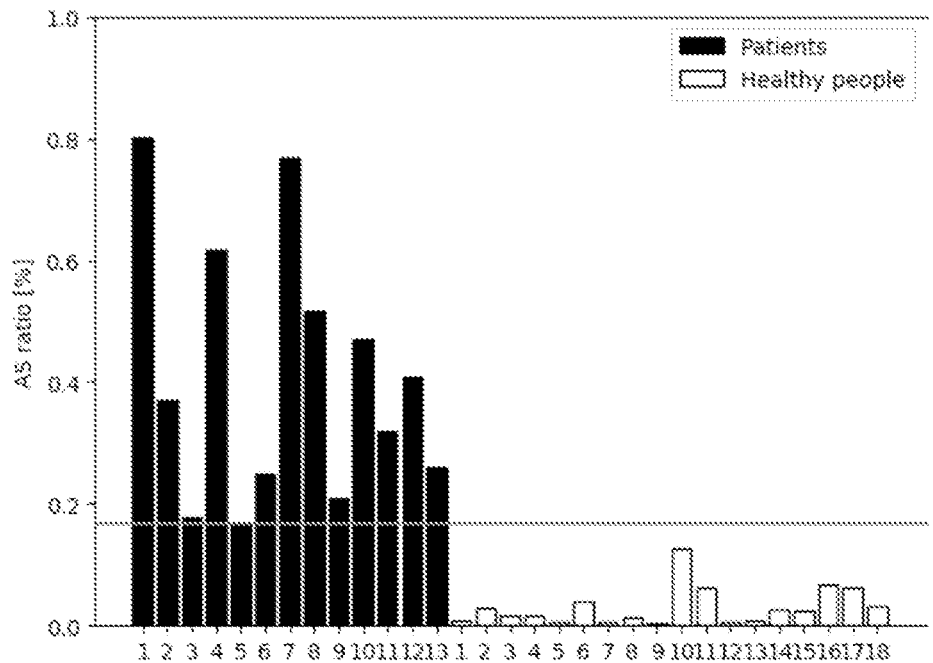
FIG. 7A shows a determination result according to a first technique in the evaluation test.
Figure 7B:
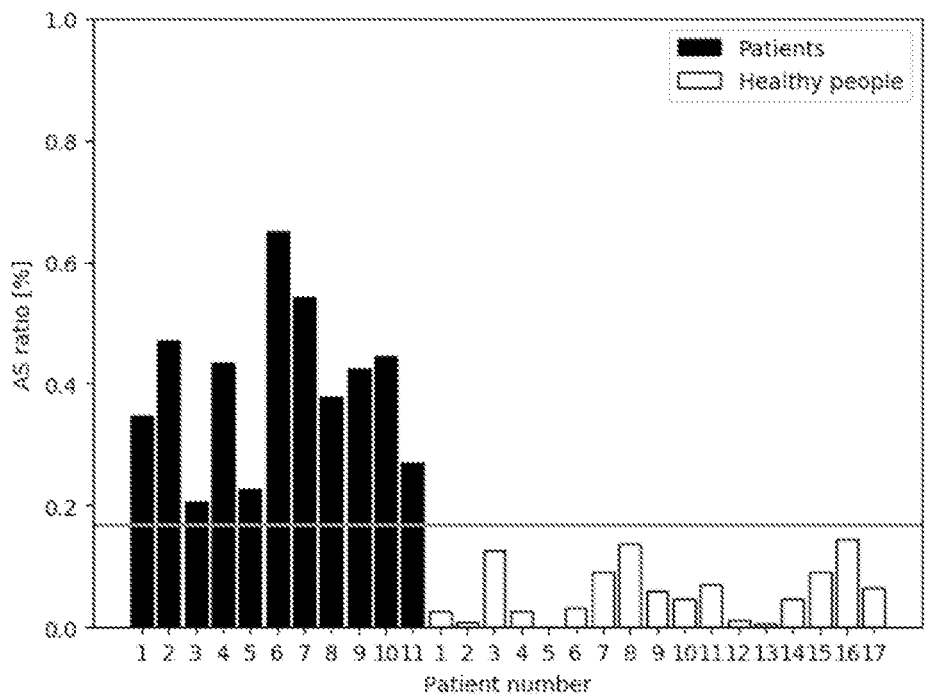
FIG. 7B shows a determination result according to a first technique in the evaluation test.
Figure 8A:
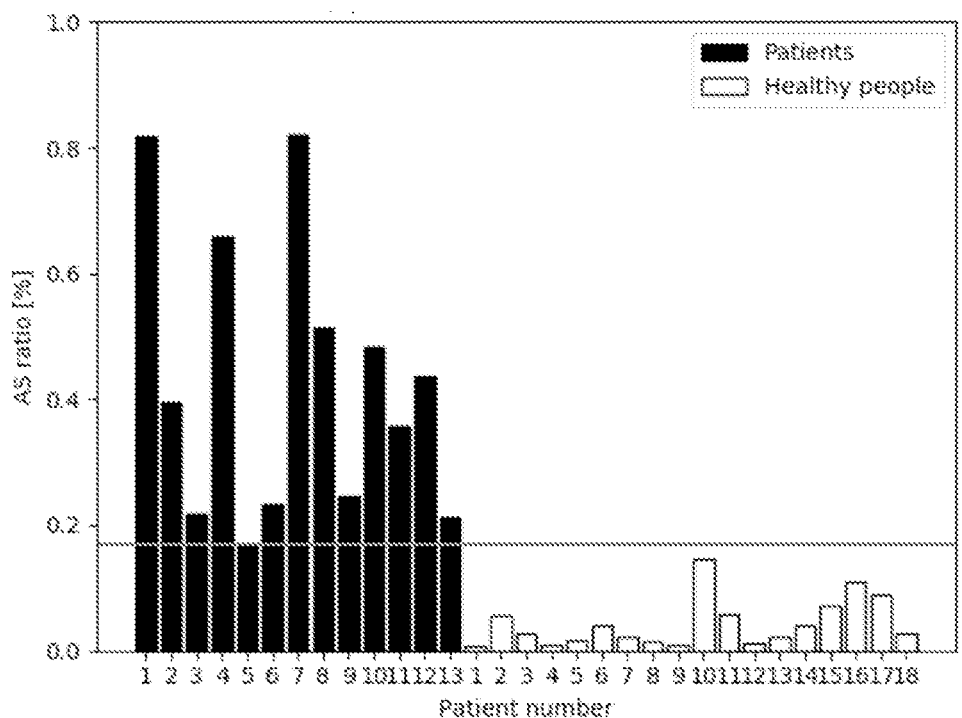
FIG. 8A shows a determination result according to a second technique in the evaluation test.
Figure 8B:
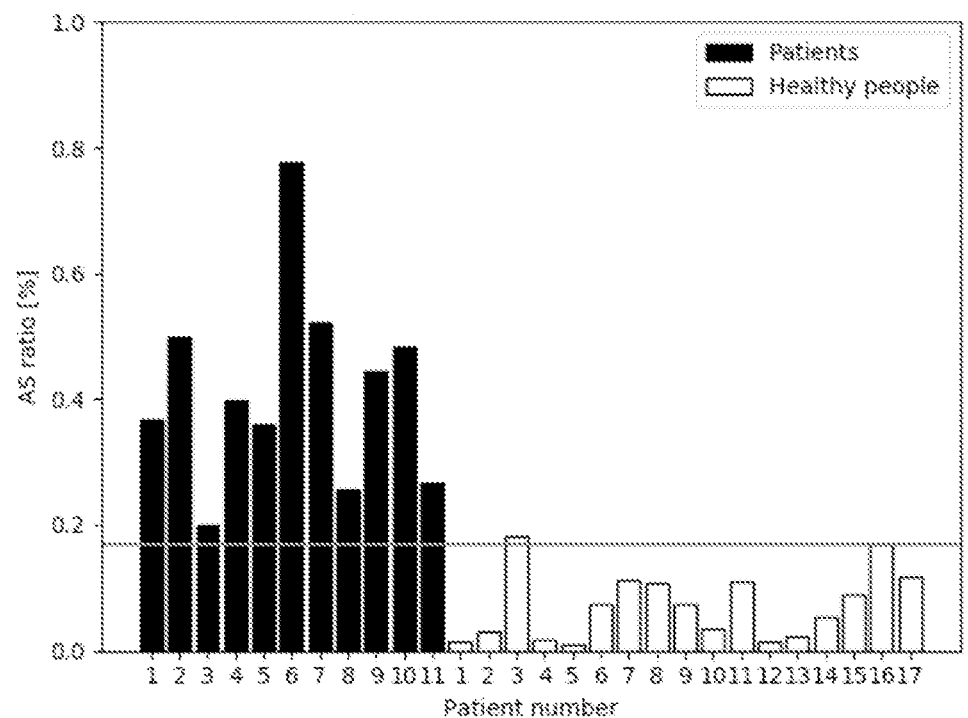
FIG. 8B shows a determination result according to a second technique in the evaluation test.
Figure 9A:
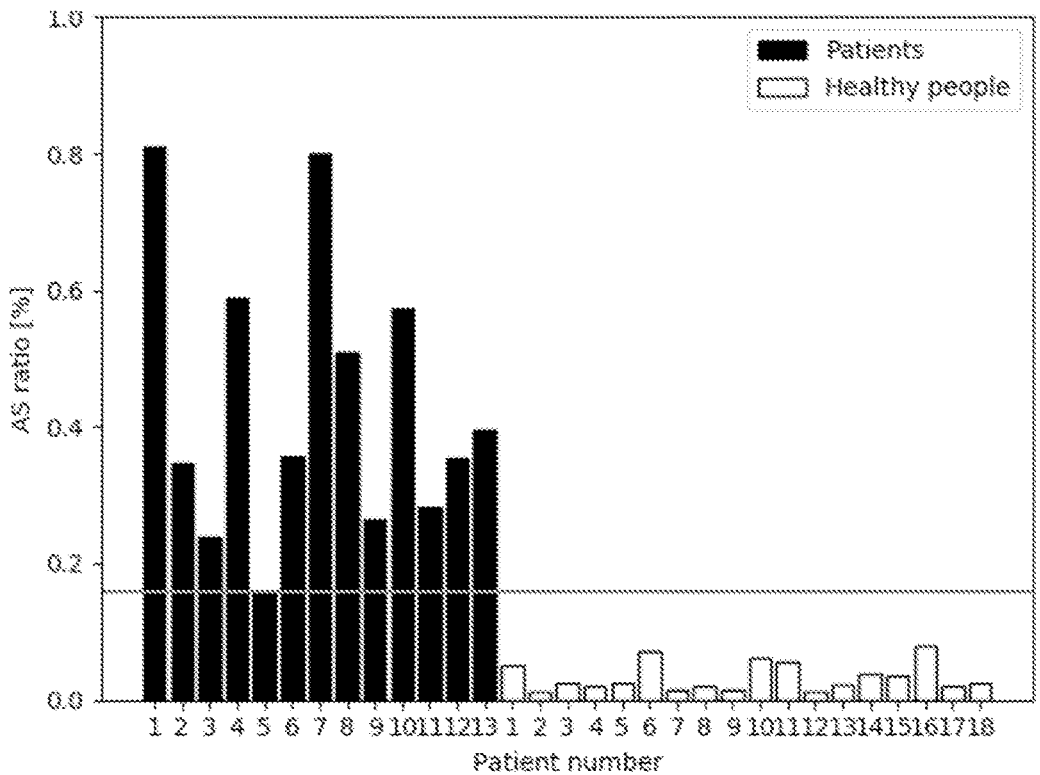
FIG. 9A shows a determination result according to a third technique in the evaluation test.
Figure 9B:
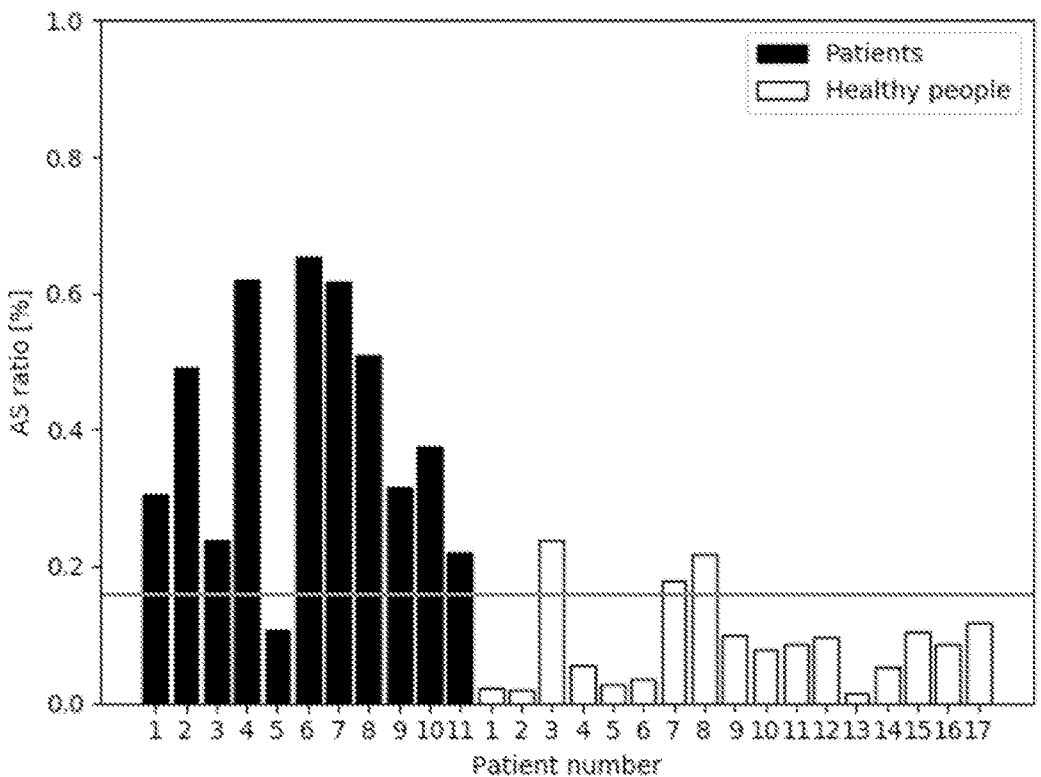
FIG. 9B shows a determination result according to a third technique in the evaluation test.
Figure 10A:
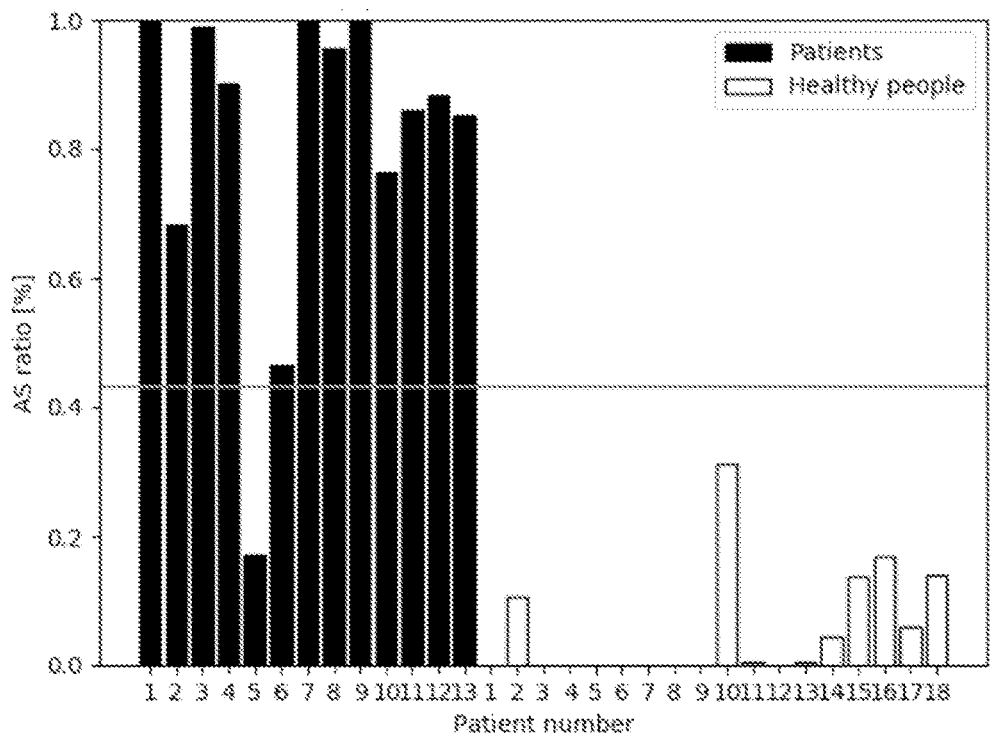
FIG. 10A shows a determination result according to a fourth technique in the evaluation test.
Figure 10B:
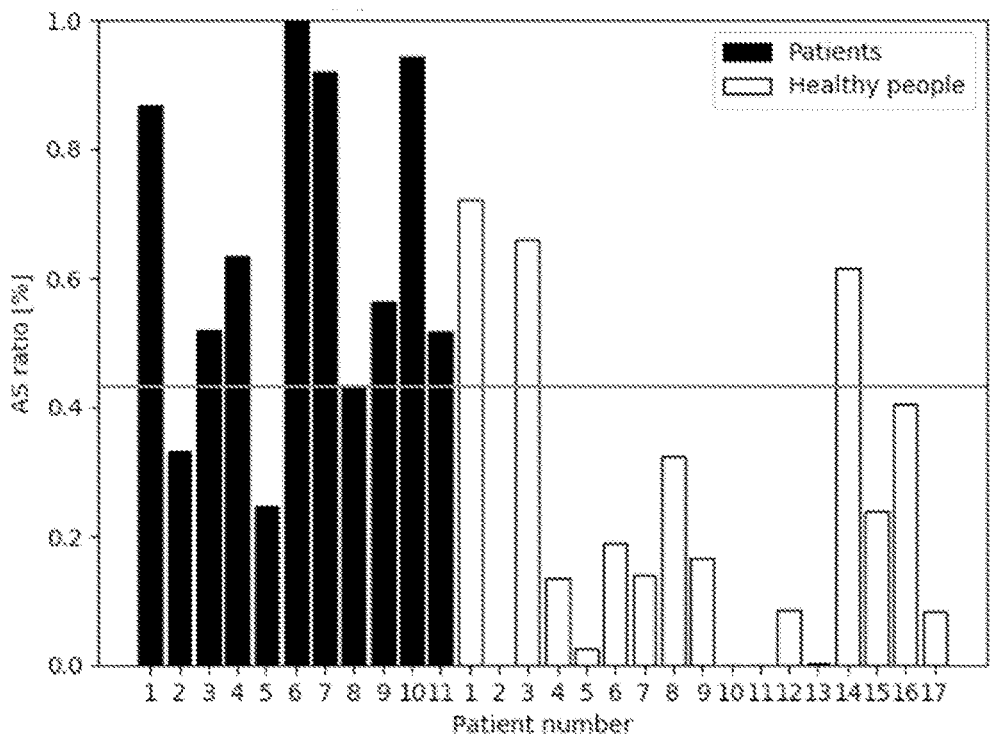
FIG. 10B shows a determination result according to a fourth technique in the evaluation test.
Figure 11A:
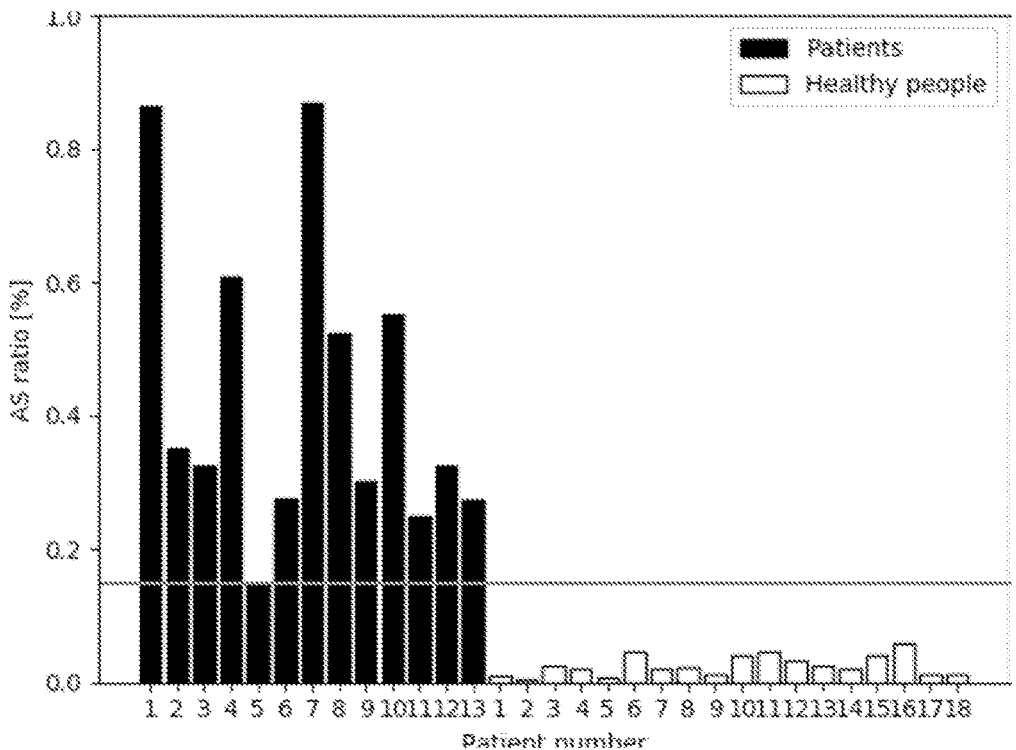
FIG. 11A shows a determination result according to a fifth technique in the evaluation test.
Figure 11B:
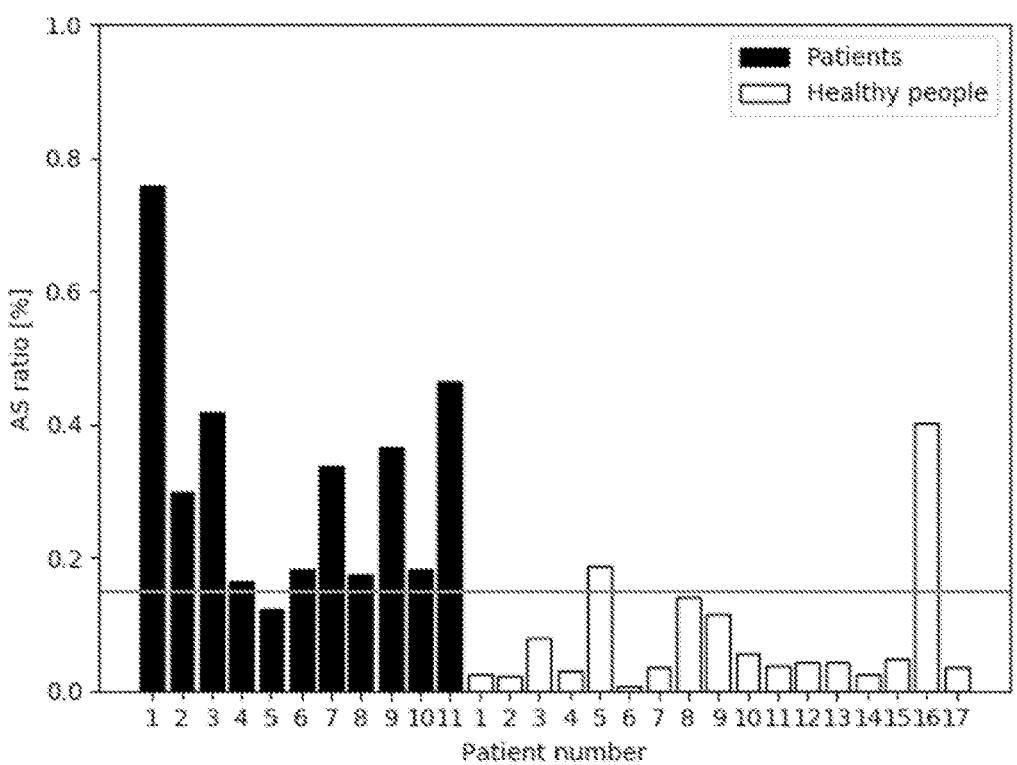
FIG. 11B shows a determination result according to a fifth technique in the evaluation test.

With reference to FIG. 4, RRI data of the subject P measured by the heart rate measuring instrument 2 is inputted to the determination apparatus 1 (step S101). Measurement of the heart rate by the heart rate measuring instrument 2 is performed until the subject P wakes up. In step S101, RRI data is inputted until the subject P wakes up.

The processing unit 10 of the determination apparatus 1 generates a feature vector by arranging pieces of RRI data of each identification target period in time series (step S103). At this time, the processing unit 10 compares each value (RRI) indicated by the RRI data with a threshold stored in advance, and determines whether or not the value is a normal value (step S1031). Then, with respect to each identification target period in which the values are all normal values, the processing unit 10 generates a feature vector. In addition, the processing unit 10 normalizes the RRIs in the identification target period (step S1033), and generates a feature vector using the normalized RRIs.

The processing unit 10 inputs the feature vector generated for each identification target period, to the identification model 15, which is a recurrent neural network (step S105). Accordingly, as an output value from the recurrent neural network, a value indicating whether the sleep state is the apnea state or the normal respiration state can be obtained for each identification target period.

The processing unit refers to the period ta of the apnea state with respect to the entire sleeping period t, and calculates an AS ratio A, which is the proportion of the period ta of the apnea state to the entire sleeping period t (step S107). When the AS ratio A is not less than the threshold TH stored in advance (A≥TH) (YES in step S109), the processing unit 10 outputs a determination result that the subject P has SAS (SAS patient) (step S111). When the AS ratio A is less than the threshold TH (A<TH) (NO in step S109), the processing unit 10 outputs a determination result that the subject P is normal (non-SAS patient) (step S113).

In a case where the determination apparatus 1 is connected to an output apparatus such as a display apparatus, the determination result in step S111 or step S113 may be transmitted to the output apparatus. Accordingly, the determination result indicating whether or not the subject P has SAS can be known through an output such as a display on the output apparatus. Alternatively, the determination result may be transmitted from the communication unit 30 to another apparatus. Examples of another apparatus include a wearable terminal of the subject P, a server apparatus of a medical institution, and the like. Accordingly, the determination result indicating whether or not the subject P has SAS can be known by use of the other apparatus.

[3. Evaluation Test]

The inventors conducted an evaluation test using clinical data in order to evaluate performance of the determination method (hereinafter, referred to as "proposed technique") of sleep apnea syndrome according to the above embodiment. In the evaluation test, determination of SAS or not was performed according to a first technique to a fifth technique under the determination conditions shown in FIG. 5. The first technique to the third technique are proposed techniques and the fourth technique and the fifth technique are determination methods as comparison examples used as references for the evaluation.

In FIG. 5, an "input value" indicates a value used as an input to the identification model, and an "identification model" indicates an identification model used for identifying the sleep state in a predetermined period. An "input method" indicates an RRI measurement method used in generation of a feature vector.

In the first technique to the third technique, as the "input value", the feature vector was generated from RRI data and inputted to an identification model that was a recurrent neural network (RNN). The identification model of each of the first technique and the third technique was LSTM among RNNs. For the identification model of the second technique, Simple RNN was used as another example of RNN. The feature vector in each of the first technique and the second technique was a variable length vector that used consecutive RRIs obtained from a fixed identification target period. The length of the identification target period was set to 60 seconds.

The feature vector in the third technique was a fixed length vector that used a fixed number of consecutive RRIs. The fixed number was set to 60 of immediately before the calculation. In the first technique to the third technique, for obtainment of the feature vector, normal value determination was performed on RRIs, and a feature vector obtained from RRIs of each identification target period of which the RRIs were all normal values was inputted to the identification model.

The fourth technique was a determination technique using a support vector machine (SVM), adopted in PATENT LITERATURE 1 above, that discriminates between the apnea state and the normal respiration state when given an HRV index. The fifth technique was a technique in which the identification model used in the fourth technique was changed from SVM to RNN used in the proposed techniques. The fifth technique was also a technique in which the input value to the identification model was changed from RRI in the first technique to the HRV index.

In the fourth technique and the fifth technique, the HRV index, which was different from RRI, was inputted to the identification model. The HRV index inputted to the identification model was all of (1) to (11) described above.

The identification model of the fourth technique was SVM, which was different from RNN, as described in PATENT LITERATURE 1. In the fourth technique, as described in PATENT LITERATURE 1, the heart rate for three minutes was measured and a feature vector formed from a plurality of HRV indexes calculated at each calculation was inputted to SVM. At this time, in the fourth technique, normal value determination regarding the measured heart rate was not performed.

In the fifth technique, similar to the generation of the feature vector according to the first technique, a continuous HRV index was calculated from consecutive RRIs measured in a first fixed period (here, 180 seconds) to be used as a feature vector, and the feature vector was inputted to LSTM for each second fixed period (60 seconds). Also in the fifth technique, normal value determination was performed on the measured RRIs, and an HRV index obtained from RRIs of each fixed period of which the RRIs were all normal values was inputted to the identification model.

Through the first technique to the fifth technique, results shown in FIG. 7A to FIG. 11B were obtained, respectively. FIGS. 7A, 8A, 9A, 10A, and 11A shows the AS ratio of each subject during learning performed by the identification model, respectively, and FIGS. 7B, 8B, 9B, 10B, and 11B shows the AS ratio of each subject as a determination result obtained by using the learned identification model, respectively. During the learning performed by the identification model, a threshold of the AS ratio between the SAS patient and the non-SAS patient was set. This threshold was used in the determination process.

Learning and determination of the identification model were performed by using electrocardiographic measurement results of a group of subjects whose attributions are shown in FIG. 6. The subjects whose RRI data was measured and used in learning by the identification model according to each determination method were composed of 13 SAS patients and 18 non-SAS patients. The subjects whose RRI data was measured and used in the determination process were composed of 11 SAS patients and 17 non-SAS patients. An "AHI (Apnea Hypopnea Index) shown in FIG. 6 is an index of severity of SAS, and is defined as the number of times of occurrence of the apnea state of not less than 10 seconds per hour. When AHI≥15, SAS is diagnosed.

From the determination results shown in FIGS. 7B, 8B, 9B, 10B, and 11B, evaluation values in each test were calculated as shown in FIG. 12. The evaluation values shown in FIG. 12 are a sensitivity SE, a specificity SP, a positive reaction predictive value PO, and a negative reaction predictive value NE, which are represented by formulas (1) to (4) below. In formulas (1) to (4), "a" represents the number of subjects who are SAS patients and "positive", "b" represents the number of subjects who are non-SAS patients and "positive", "c" represents the number of subjects who are SAS patients and "negative", and "d" represents the number of subjects who are non-SAS patients and "negative". Here, the "positive" is defined as corresponding to a subject whose AS ratio is greater than the threshold" (e.g., AS≥threshold TH, or AS>threshold TH), and the negative" is defined as corresponding to a subject whose AS ratio is smaller than the threshold (e.g., AS<threshold TH, or AS≤threshold TH).

$$SE[\%]=a/(a+c)\times 100 \quad \text{formula (1)}$$

$$SP[\%]=d/(b+d)\times 100 \quad \text{formula (2)}$$

$$PO[\%]=a/(a+b)\times 100 \quad \text{formula (3)}$$

$$NE[\%]=d/(c+d)\times 100 \quad \text{formula (4)}$$

With reference to FIG. 12, when the first technique to the third technique are compared with the fourth technique, the evaluation values of the first technique to the third technique are each higher than those of the fourth technique. The fourth technique is a determination technique, in PATENT LITERATURE 1 above, that uses a support vector machine that discriminates between the apnea state and the normal respiration state when given an HRV index. Therefore, the first technique to the third technique each have a determination accuracy higher than that of the conventional determination technique. That is, it has been verified that the determination method (the first technique to the third technique) that performs a determination process using an identification result obtained by inputting, to RNN, a feature vector composed of RRIs consecutive in time series is more effective than the conventional determination method using an identification result obtained by inputting the HRV index to SVM.

In particular, the first technique and the second technique each have a very high accuracy, with each evaluation value exceeding 90%. Further, the first technique has a significantly high accuracy, with all evaluation values being 100%. That is, when LSTM, in particular, among RNNs is used as the identification model, the determination accuracy can be significantly improved. Therefore, it has been verified that the first technique and the second technique are especially effective when compared with the conventional determination method.

It should be noted that the third technique is a technique in which the generation method of the feature vector is changed from the variable length vector in the first technique vector to a fixed length vector. When the evaluation values of these techniques are compared, the values according to the first technique are significantly higher than those according to the third technique. Therefore, the determination accuracy is higher when the variable length vector is used as the feature vector than when the fixed length vector is used as the feature vector. Therefore, it has been verified that, as the feature vector, the variable length vector is more effective than the fixed length vector.

The evaluation values of the first technique and the second technique among the first technique to the third technique are each significantly higher than those of the fifth technique, and thus, the first technique and the second technique each have a higher determination accuracy than the fifth technique. Therefore, it has been verified that, even if the identification model is changed from SVM to RNN in the fourth technique, the first technique and the second technique, which are the proposed techniques, are especially effective.

The first technique and the fifth technique are different from each other only in that the input to the LSTM as the identification model is RRI and the HRV index, respectively. The evaluation values of the first technique are all significantly higher than those of the fifth technique, and thus, the first technique has a higher determination accuracy than the fifth technique. Therefore, it has been verified that, as the input to LSTM, RRI is more effective than the HRV index. Further, as for the second technique, since the identification model is Simple RNN, which is an RNN but different from the RNN used in the first technique, the second technique has a slightly lower determination accuracy than the first technique, but the evaluation values of the second technique are all higher than those of the fifth technique. Therefore, it has been verified that, as the input, RRI is more effective than the HRV index not only for LSTM but also for RNN.

The present invention is not limited to the above embodiment and various modifications can be made.

REFERENCE SIGNS LIST 1 sleep apnea determination apparatus (determination apparatus)
2 heart rate measuring instrument
10 processing unit
11 generation unit
12 normal value determination unit
13 standardization processing unit
14 identification unit
15 identification model
16 calculation unit
17 determination unit
20 storage device
21 computer program
21A electrode
30 communication unit
100 system
A AS ratio
FV1 feature vector
FV2 feature vector
I signal intensity
P subject
T1 period
T2 period
TH threshold

The invention claimed is:

1. A sleep apnea syndrome determination apparatus comprising: a heart rate measuring instrument configured to be attached to a body of a subject, wherein the heat rate measuring instrument measures an electrocardiographic signal of the subject using a plurality of electrodes and RRI data indicating a heart rate interval (R-R Interval; RRI) of about a second based on the electrocardiographic signal; a memory; a processing unit coupled to the memory and configured to, by using the RRI data in a sleeping period of a subject, determine whether or not the subject has sleep apnea syndrome, wherein each of the RRI data is received from the heat rate measuring instrument connected to the processing unit, and wherein the processing unit performs operations comprising receiving each of the RRI data from the heart rate measuring instrument via a communication unit coupled to the processing unit, comparing each of the RRI data to a normal value threshold related to RRI, determining whether each of the RRI data is a normal RRI value or an abnormal RRI value based on the comparison, instantaneously generating a feature vector including a plurality of heart rate intervals that are consecutive in the sleeping period, wherein the feature vector is a variable length vector formed as a time series of a group of pieces of the normal RRI data having normal values respectively indicating the plurality of heart rate intervals in an identification target period having a fixed period length of about 60 seconds, wherein the variable length vector does not include the abnormal RRI value, and wherein a number of elements of the variable length vector is variable, not generating the variable length vector if the abnormal RRI value within the RRI data is determined, inputting the variable length vector formed as the time series of the group of pieces of the normal RRI data as the feature vector to the processing unit operating as a recurrent neural network trained through machine learning in advance so as to output, in response to the variable length vector having been inputted, a value indicating a sleep state in the identification target period, calculating, from the value that is outputted as a result of inputting each variable length vector generated for the sleeping period to the recurrent neural network and that is obtained for each identification target period within the sleeping period that corresponds to the plurality of heart rate intervals included in the variable length vector inputted, an index based on a ratio between a period of an apnea state and a period of a normal respiration state in the sleeping period, and determining whether or not the subject has sleep apnea syndrome, on the basis of the index as compared to a threshold related to the sleep apnea syndrome, wherein the recurrent neural network is a Long Short-Term Memory (LSTM) network configured to input the variable length vector as the feature vector.

2. The sleep apnea syndrome determination apparatus according to claim 1, wherein the generating of the variable length vector includes standardizing a value of each of the plurality of heart rate intervals.

3. The sleep apnea syndrome determination apparatus according to claim 1, wherein the index is a ratio of the period of the apnea state to the sleeping period, and the determining includes determining that, when the ratio is greater than threshold indicating sleep apnea syndrome, the subject has sleep apnea syndrome.

4. The sleep apnea syndrome determination apparatus according to claim 1, wherein the abnormal RRI value corresponds to an artifact.

5. A sleep apnea syndrome determination method for, by using RRI data indicating a heart rate interval in a sleeping period of a subject, determining whether or not the subject has sleep apnea syndrome, the sleep apnea syndrome determination method comprising: a step of receiving the RRI data from a heart rate measuring instrument attached to a body of the subject, wherein the heart rate measuring instrument measures an electrocardiographic signal of the subject using a plurality of electrodes and RRI data indicating a heart rate interval (R-R Interval; RRI) of about a second based on the electrocardiographic signal for a sleeping period of the subject, a step of receiving each of the RRI data from the heart rate measuring instrument via a communication unit connected to a processing unit; a step of comparing each of the RRI data to a normal value threshold related to RRI; a step of determining whether each of the RRI data is a normal RRI value or an abnormal RRI value based on the comparison; a step of instantaneously generating a feature vector including a plurality of heart rate intervals that are consecutive in the sleeping period, wherein the feature vector is a variable length vector formed as a time series of a group of pieces of the normal RRI data having normal values respectively indicating the plurality of heart rate intervals in an identification target period having a fixed period length of about 60 seconds, wherein the variable length vector does not include the abnormal RRI value, and wherein a number of elements of the variable length vector is variable; a step of not generating the variable length vector if the abnormal RRI value within the RRI data is determined; a step of inputting the variable length vector formed as the time series of the group of pieces of the normal RRI data as the feature vector to the processing unit operating as a recurrent neural network trained through machine learning in advance so as to output, in response to the variable length vector having been inputted, a value indicating a sleep state in the identification target period, wherein the recurrent neural network is a Long Short-Term Memory (LSTM) network configured to input the variable length vector as the feature vector; a step of calculating, from the value that is outputted as a result of inputting each variable length vector generated for the sleeping period to the recurrent neural network and that is obtained for each identification target period within the sleeping period that corresponds to the plurality of heart rate intervals included in the variable length vector inputted, an index based on a ratio between a period of an apnea state and a period of a normal respiration state in the sleeping period; a step of determining whether or not the subject has sleep apnea syndrome, on the basis of the index as compared to a threshold related to the sleep apnea syndrome; and a step of displaying a result of determining whether the subject has sleep apnea syndrome on a display coupled to the processing unit.

6. A sleep apnea syndrome determination program configured to cause a computer to execute a process of, by using RRI data indicating a heart rate interval in a sleeping period of a subject, determining whether or not the subject has sleep apnea syndrome, the sleep apnea syndrome determination program comprising: a step of receiving the RRI data from a heart rate measuring instrument attached to a body of the subject, wherein the heart rate measuring instrument measures an electrocardiographic signal of the subject using a plurality of electrodes and RRI data indicating a heart rate interval (R-R Interval; RRI) of about a second based on the electrocardiographic signal for a sleeping period of the subject, a step of receiving each of the RRI data from the heart rate measuring instrument via a communication unit connected to a processing unit; a step of comparing each of the RRI data to a normal value threshold related to RRI; a step of determining whether each of the RRI data is a normal RRI value or an abnormal RRI value based on the comparison; a step of instantaneously generating a feature vector including a plurality of heart rate intervals that are consecutive in the sleeping period, wherein the feature vector is a variable length vector formed as a time series of a group of pieces of the normal RRI data having normal values respectively indicating the plurality of heart rate intervals in an identification target period having a fixed period length of about 60 seconds, wherein the variable length vector does not include the abnormal RRI value, and wherein a number of elements of the variable length vector is variable; a step of not generating the variable length vector if the abnormal RRI value within the RRI data is determined; a step of inputting the variable length vector formed as the time series of the group of pieces of the normal RRI data as the feature vector to the processing unit operating as a recurrent neural network trained through machine learning in advance so as to output, in response to the variable length vector having been inputted, a value indicating a sleep state in the identification target period, wherein the recurrent neural network is a Long Short-Term Memory (LSTM) network configured to input the variable length vector as the feature vector; a step of calculating, from the value that is outputted as a result of inputting each variable length vector generated for the sleeping period to the recurrent neural network and that is obtained for each identification target period within the sleeping period that corresponds to the plurality of heart rate intervals included in the variable length vector inputted, an index based on a ratio between a period of an apnea state and a period of a normal respiration state in the sleeping period; a step of determining whether or not the subject has sleep apnea syndrome, on the basis of the index as compared to a threshold related to the sleep apnea syndrome; and a step of displaying a result of determining whether the subject has sleep apnea syndrome on a display coupled to the processing unit.

* * * * *